United States Patent [19]

Kosako

[11] Patent Number: 5,527,714

[45] Date of Patent: Jun. 18, 1996

[54] PROCESS FOR DETERMINING CONCENTRATION OF AN ANALYTE IN A SAMPLE BY ANTIGEN/ANTIBODY MEDIATED PARTICLE AGGLUTINATION IN THE PRESENCE OF INSOLUBLE CONTAMINATS

[75] Inventor: Tatsuya Kosako, Akashi, Japan

[73] Assignee: Toa Medical Electronics Co., Ltd., Kobe, Japan

[21] Appl. No.: 283,634

[22] Filed: Aug. 1, 1994

Related U.S. Application Data

[63] Continuation of Ser. No. 672,094, Mar. 19, 1991, abandoned.

[30] Foreign Application Priority Data

Mar. 28, 1990 [JP] Japan .................................. 2-081749

[51] Int. Cl.⁶ ................................................. G01N 33/546
[52] U.S. Cl. .................... 436/534; 356/335; 356/336; 422/73; 436/536; 436/538; 436/805
[58] Field of Search ................... 356/335, 336; 422/73; 436/534, 536, 538, 805

[56] References Cited

U.S. PATENT DOCUMENTS

| | | | |
|---|---|---|---|
| 4,521,521 | 6/1985 | Abbott et al. | 436/805 |
| 4,851,329 | 7/1989 | Cohen et al. | 436/805 |
| 4,929,079 | 5/1990 | Delfour et al. | 356/336 |

OTHER PUBLICATIONS

MacDonald et al, *Cytometry*, Jul. 1982, 3(1), pp. 55–58 (Abstract).

*Primary Examiner*—James C. Housel
*Assistant Examiner*—Christopher L. Chin
*Attorney, Agent, or Firm*—Morrison Law Firm

[57] ABSTRACT

Particle size distributions with greatly improved accuracy are prepared for diagnostic analysis using antigen/antibody reactions to concentrate sensitized insoluble carriers into non-aggregated and aggregated particles of known size. The analyte is analyzed by an electronic analyzer to determine the quantity and size distribution of concentrated non-aggregated and aggregated insoluble carriers resulting from the antigen/antibody reaction, as well as spurious particles that may be present in the analyte. The concentrated non-aggregated and aggregated insoluble carriers occur in known regions of the measured size distribution. The spurious particles exist throughout the size distribution. The distribution of spurious particles is determined in the regions where the desired particles are known to be absent. A complete distribution of spurious particles is constructed by interpolation using a cubic spline function. The initial measured size distribution is corrected by subtracting the interpolated spurious particle distribution from the initial size distribution.

3 Claims, 11 Drawing Sheets

PROCESS FOR DETERMINING CONCENTRATION OF AN ANALYTE IN A SAMPLE BY ANTIGEN/ANTIBODY MEDIATED PARTICLE AGGLUTINATION IN THE PRESENCE OF INSOLUBLE CONTAMINATS

This is a continuation application of application Ser. No. 07/672,094, filed Mar. 19, 1991, now abandoned.

BACKGROUND OF THE INVENTION

This invention relates to analysis of a sample. More particularly, the invention relates to the analysis of a sample obtained for the diagnosis of a disease. Still more particularly, the invention relates to analysis of a sample by means of antigen/antibody mediated agglutination reactions.

The use of antigen/antibody reactions to prepare an analyte for diagnosis is well known and is commonly used with such analytical procedures as radio immunoassay and enzyme immunoassay. Both of these procedures use antigen/antibody reactions to bind an analyte to a detectable marker. The amount of marker that is bound to the analyte directly correlates with the amount of analyte in the sample and becomes an index of the presence or extent of a disease. For example, a tumor. Problems associated with these methods include the preparation time requirement of the analyte, and the safe disposal of the analyte.

A proposed counting immunoassay method uses antigen/antibody reactions in the preparation of the analyte. These antigen/antibody reactions detect by aggregation even small percentages of the analyte of interest in the sample with improved sensitivity and decreased sample preparation time.

In this method, a sample containing the antigen to be measured is mixed with insoluble carriers that are sensitized with the multivalent specific antibody for the subject antigen. These carriers are, for example, made up of micron sized latex particles. The reaction between the antigens in the sample and the antibodies bound to the latex particles causes the reacted carriers to aggregate. Measuring the number of total carriers, in comparison with the number and degree of aggregation of carriers, determines the concentration of the antigen in the sample. A major problem of this method is that the analyte may be contaminated with spurious particles, such as chylous particles, cell fragments or the like, that decrease the accuracy of the measurement. These spurious particles cannot be differentiated if they fall within the size range of the non-aggregated and aggregated insoluble carriers. The presence of the spurious particles greatly reduces the reliability and accuracy of the measurements. It is possible to eliminate the spurious particles from the sample prior to measurement, but this requires a substantial amount of preprocessing.

OBJECTS AND SUMMARY OF THE INVENTION

It is an object of the invention to provide a process for recording and measuring carrier particle size distributions that overcomes the drawbacks of the prior art.

It is a further object of the invention to provide a process for accurately recording and measuring carrier particle size distributions even in the presence of spurious particles.

Briefly stated, the present invention provides apparatus and method for determining particle size distributions with greatly improved accuracy using antigen/antibody reactions to concentrate sensitized insoluble carriers into non-aggregated and aggregated particles of known size. The analyte is analyzed by an electronic analyzer to determine the quantity and size distribution of concentrated non-aggregated and aggregated insoluble carriers resulting from the antigen/antibody reaction, as well as spurious particles that may be present in the analyte. The concentrated non-aggregated and aggregated insoluble carriers in known regions of the measured size distribution. The spurious particles exist throughout the size distribution. The distribution of spurious particles is determined in the regions where the desired particles are known to be absent. A complete distribution of spurious particles is constructed by interpolation using for example a cubic spline function. The initial measured size distribution is corrected by subtracting the interpolated spurious particle distribution resulting in a corrected size distribution.

According to an embodiment of the invention, there is provided apparatus for preparing a corrected size distribution of desired particles in a sample comprising: means for detecting particles in the analyte to produce a particle detection signal, means, responsive to the particle detection signal, for determining a size of the particles, means, responsive to the size, for determining a total distribution of sizes of the particles in the sample, means for determining a distribution of spurious particle sizes within the total distribution, and means for subtracting the distribution of spurious particle sizes from the total distribution of sizes to produce a corrected distribution of the desired particles.

According to a feature of the invention, there is provided a method for preparing a corrected distribution of desired particles in an analyte comprising: detecting particles in the analyte to produce a particle detection signal, determining a total distribution of sizes of the particles in the analyte, determining a distribution of spurious particle sizes within the total distribution of sizes, and subtracting the distribution of spurious particle sizes from the total distribution of sizes to produce a corrected distribution of the desired particles.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
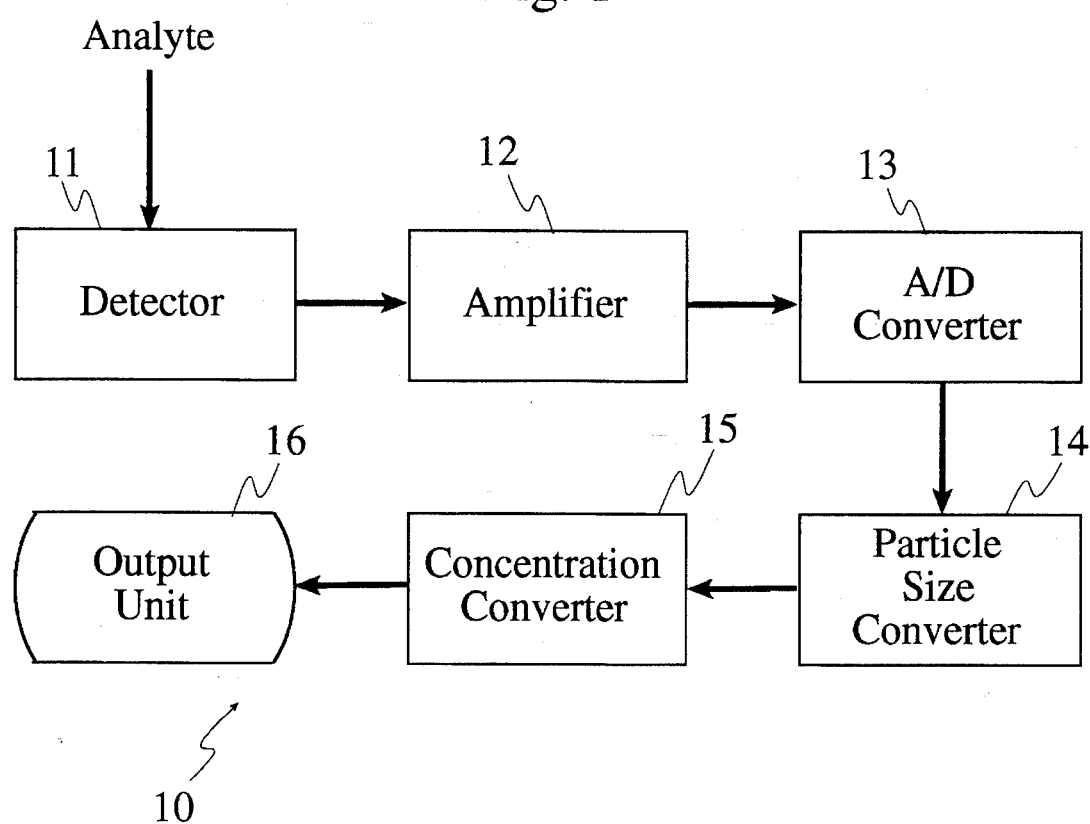
FIG. 1 is a block diagram of an antigen concentration analyzing means.

Referring to FIG. 1 an analyzer 10, includes a detector 11 that converts the relative sizes of particles in a sample into an electrical signal for analysis and measurement. The electrical signal output of detector 11 is connected to an amplifier 12, where it is amplified for conversion to a digital message by an A/D converter 13. The digital message output of A/D converter 13 is then read in a particle size converter 14 to determine the size distribution of particles detected. A concentration converter 15, which is connected to the output of particle size converter 14, uses the size distribution data calculated by particle size converter 14 to determine the concentration of antigen in the sample. This information is connected to an output unit 16, for output to an operator.

During operation, a prepared analyte containing a substance to be analyzed and an insoluble carrier that is sensitized with a specific antibody for the suspected antigen is presented to detector 11 of analyzer 10. Detector 11 converts the non-aggregated and aggregated carriers within the analyte into analog electrical signals that represent the quantity and respective sizes of all of the particles detected, both desired and spurious. The output of detector 11 is amplified by amplifier 12 and presented to A/D converter 13 for conversion to a digital message for further processing. The digital information is read by particle size converter 14 to determine the particle size distribution in the analyte for conversion into concentration data by concentration converter 15. The resultant concentration of antigen is then output by output unit 16 for interpretation by a user.

The embodiment of the invention shown in FIG. 1 may be realized using any suitable hardware, software, or combination thereof. For purposes of illustration, detector 11 is a flow cell of a type that flows the analyte past a conventional optical detector using, for example, a laser at one side of the flow cell, and an optical detector detecting the amplitude of received laser light at the other side of the flow cell. The flow cell is of a conventional type which forces the particles in the analyte to move in a flattened flow past the laser/detector combination.

A/D converter 13 is a conventional device that detects and holds the peak values of the analog signal and digitizes the resulting values for processing in subsequent circuits.

Particle size distribution converter 14 includes a conventional memory unit for storing the digital values produced by A/D converter 13, and a microcomputer for reading out and processing the stored digital values. The functions of concentration converter 15, and, optionally, output unit 16, also may be performed by the microcomputer. Other types of processing devices such as, for example, a mainframe computer, or a special purpose computer may be substituted for the microcomputer without departing from the spirit and scope of the invention.

It is believed that all of the above apparatus is conventional, and its construction and function would be immediately evident to one skilled in the art. Consequently, it is believed that further description thereof is unnecessary.

Figure 2:
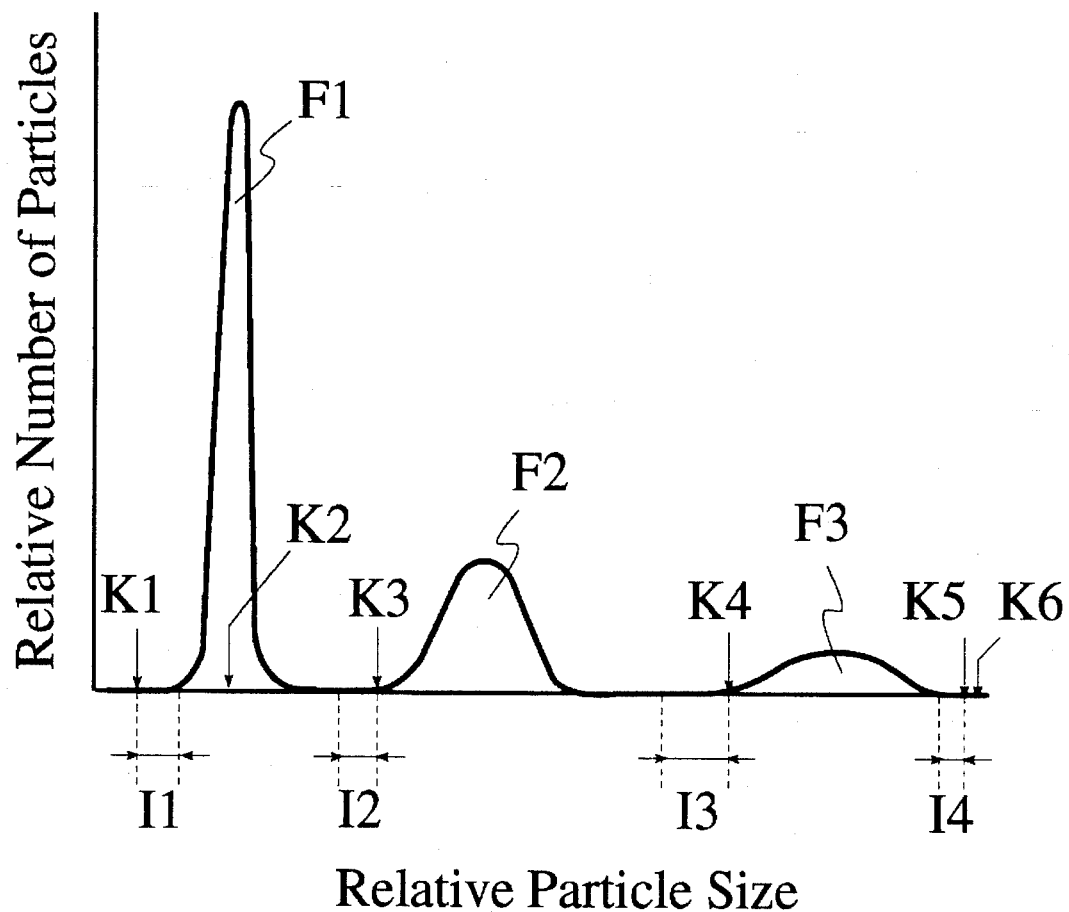
FIG. 2 is an example of a particle size distribution graph prepared by the means of FIG. 1.

FIG. 2 is a graph of the particle size distribution of insoluble carriers aggregated in a liquid medium of the sample. This aggregation is caused by a reaction between an antigen and an antibody on insoluble carriers.

In the graph, a horizontal axis represents a relative diameter of particle sizes. A vertical axis represents a relative number of particles along the horizontal axis.

In this example, an area F1 shows a distribution of non-aggregated insoluble carriers. An area F2 shows a distribution of two aggregated insoluble carriers and an area F3 shows a distribution of three aggregated insoluble carriers.

Areas on the horizontal axis of the graph that are designated with I designators represent spurious particles that fall between the ranges of the non-aggregated and aggregated carriers. I1 is an area where spurious particles are smaller than the size of non-aggregated insoluble carriers. I2 is an area where spurious particles are larger than non-aggregated, but smaller than two aggregated carriers. I3 is an area where spurious particles are larger than two aggregated carriers, but smaller than three aggregated carriers. I4 is an area where spurious particles are larger than three aggregated carriers.

Points on the horizontal axis of the graph that are designated by K1 through K6 represent spurious particles sizes. For example, K1 represents the smallest spurious particles residing in area I1 and K3 represents the largest spurious particles residing in area I2. K2 is the size of the spurious particles that are assumed to reside halfway between K1 and K3. K4 represents the largest spurious particles residing in area I3, K5 represents the largest spurious particles in area I4, and K6 represents all particles larger than K5.

According to Japanese Laid-Open patent Publications 60-111963 and 1-259257, the degree of aggregation is defined as $$A = P/(M+P) = P/T,$$

where

M is the number of non-aggregated insoluble carrier particles,

P is the number of aggregated insoluble carrier particles, and

T is the total number of particles.

The value of P and M, respectively, is obtained by classifying the distribution of particle sizes.

In the previously mentioned CIA method, spurious particles in the sample can appear in the particle distribution of the insoluble carriers being measured. However, the CIA method cannot differentiate spurious particles falling within the size ranges (F1, F2, and F3) of the insoluble carriers.

To derive an accurate representation of the distribution of non-aggregated and aggregated insoluble carriers, it is necessary to account for and discard the spurious particles that fall within areas F1, F2, and F3 of the graph. Because the distribution of spurious particles in areas I1 through I4 is clearly seen, it is possible to interpolate, for example by means of a spline function, the distribution of spurious particles in area F1, F2 and F3. By subtracting the interpolated distribution of spurious particles from the values shown for areas F1, F2, and F3 it is possible to derive an accurate size distribution analysis of the desired non-aggregated and aggregated insoluble carriers.

Figure 3:
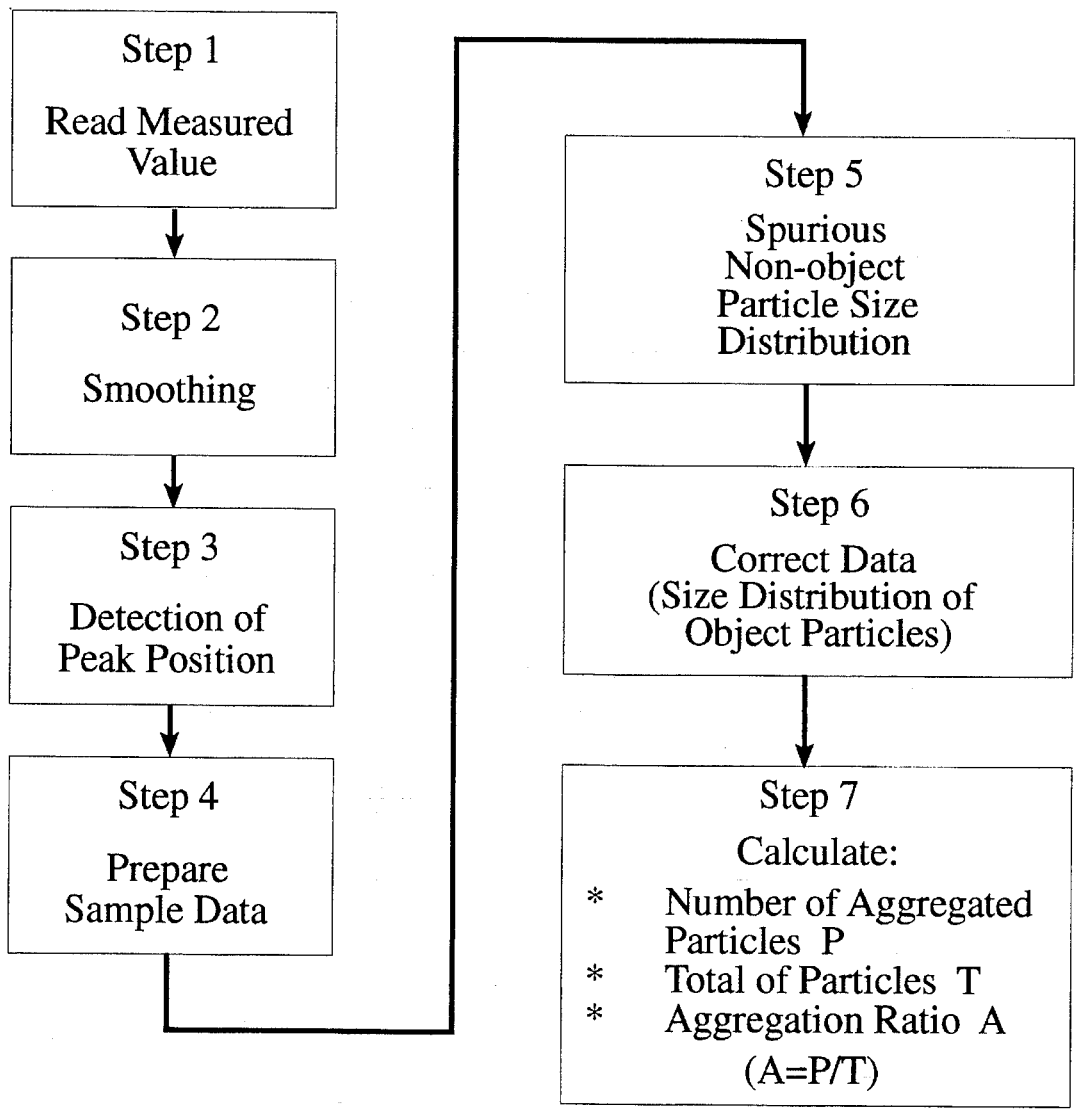
FIG. 3 is a flow chart of a conversion process for preparing a particle size distribution according to the present invention.

Referring to FIGS. 2 and 3, step 1 of the present invention reads out the values determined by analyzer 10 (FIG. 1). This includes the values for non-aggregated and aggregated carriers as well as for spurious particles that fall within their pertinent size ranges. Step 2 smoothes the curves of the readout values to eliminate statistical errors. Step 3 detects a peak position in a distribution of non-aggregated particles (F1) of the smoothed readout and determines respective areas I1 through I4 (areas containing only spurious particles). Step 4 prepares sample data from the size distribution of the spurious particles of areas, I1 through I4. Step 5 determines the spurious particle size distribution over the entire range of the analyte using a cubic spline function interpolation of the sample derived in step 4. Step 6 corrects the readout of step 2 by subtracting the interpolated size distribution of the spurious particles from F1 through F4. Step 7 calculates the degree of aggregation A using $A=P/T$, where P and T are corrected values developed in step 6.

To determine the size distribution of the spurious particles, each of the areas (I), are divided into a number of channels, and the spurious particles in each channel are counted. These counts are converted into sample data as follows:

Area I1 through I4 are each divided into channels, which, for example, may be as follows: area I1, five channels; area I2, ten channels; area I3, twenty channels and area I4, twenty channels. A predetermined count is assigned to each channel. Measurement is then made of the actual number of spurious particles in each channel. If the actual numbers of particles is less than the predetermined number, the sample data is set to zero. If the actual number of particles is larger than the predetermined number, the sample data is set to the actual number.

In using the sample data of the particles within area I1 through I4, the particle size distribution of the spurious particles between these areas can be determined by a cubic spline function. Points on the horizontal axis of the graph that are designated by K1 through K6 represent spurious particle sizes. For example, K1 represents the smallest spurious particles residing in area I1 and K3 represents the largest spurious particles residing in area I2. K2 is the size of spurious particles assumed to reside halfway between K1 and K3. K4 represents the largest spurious particles residing in area I3 and K5 represents the largest spurious particles in area I4, K6 represents all particles larger than K5. With spline interpolation, K1–K5 is a knot.

In the size ranges of K6, which includes the chylous particles and the aggregated four or more insoluble carriers, it is difficult to determine the number of particles by interpolation. To determine the number of particles in these areas, the number of chyle or spurious particles is then measured before four or more insoluble carriers can be aggregated by the antigen/antibody reactions. The measured value at that point is the number of the spurious particles present.

Once the particle sizes within areas I1 through I4 and K6 have been determined, the size distribution of the spurious particles is interpolated for the entire range of sizes. The interpolated spurious particle size distribution is subtracted from the total size distributions recorded for areas F1, F2, F3 and so forth to determine the corrected size distributions of non-aggregated and aggregated insoluble carriers.

The functions shown in FIG. 3 may be performed by any suitable hardware, software or hardware/software combination. In the preferred embodiment, all of these functions are performed in a programmed digital computer and, in the most preferred embodiment, in a programmed microprocessor.

Figure 4A:
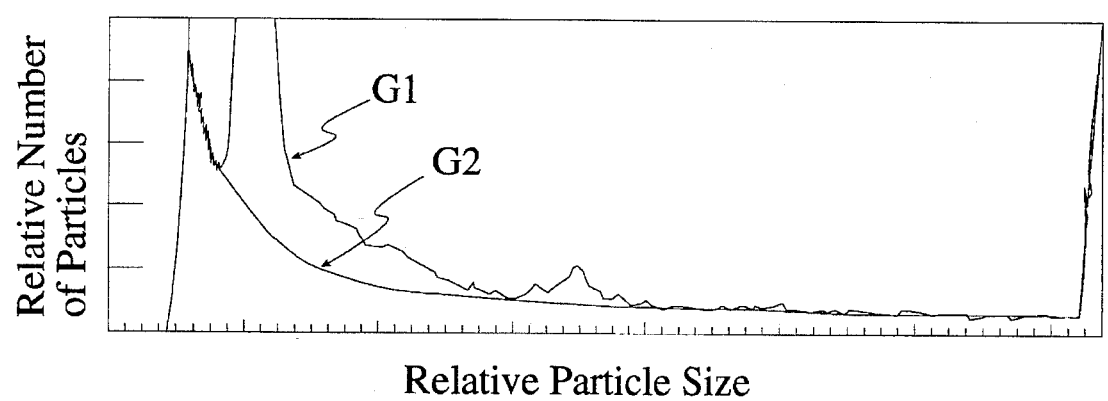
FIG. 4A is a distribution plot of the carrier particles to be measured, as well as spurious particles distributed over the entire area, according to a first example of this invention.
Figure 4B:
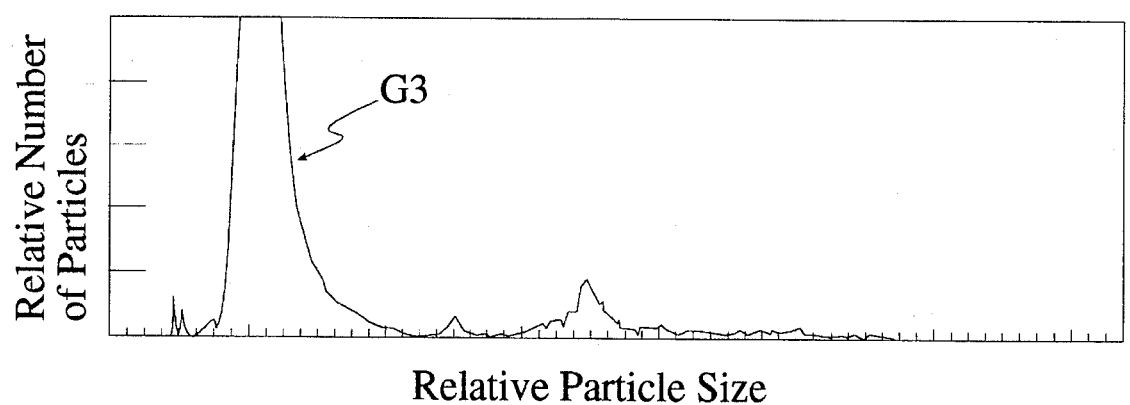
FIG. 4B is a distribution plot of only the carrier particles in the first example.

FIGS. 4A and 4B show the results of the application of the present invention. In these examples, ten microliters of antigen-containing sample was mixed with ten microliters of insoluble carrier solution prepared by sensitization of antibody and eighty microliters of reaction buffer solution. The mixture was then agitated for fifteen minutes to produce the aggregated particles. A total particle size distribution curve, G1, was then plotted. An interpolated spurious particle size distribution, curve G2 was overlaid on curve G1. Curve G2 was derived using step 5 of the present invention.

Curve G3 of FIG. 4B depicts the result of subtracting the interpolated size distribution of spurious particles (G2) from the total particle size distribution (G1) using step 6 of the present invention to derive an actual distribution of non-aggregated and aggregated insoluble carriers.

According to uncorrected distribution curve G1 (FIG. 4A), the degree of aggregation A is 4.79% and the alpha-phytoprotein (AFP) concentration of the analyte per unit volume was 19.23 ng/ml. Corrected distribution curve G3 (FIG. 4B) shows a degree of aggregation A of 1.08% and an AFP concentration of analyte per unit volume of 2.70 ng/ml.

Figure 5A:
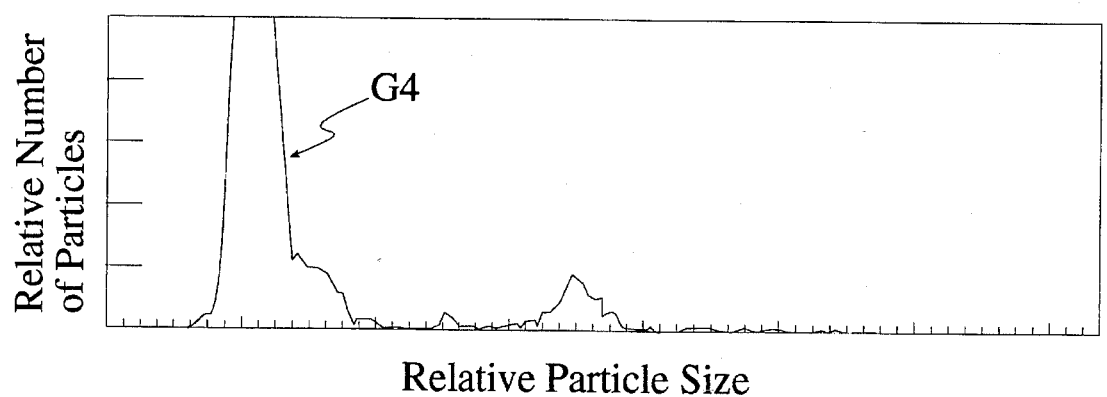
FIG. 5A is a distribution plot of the carrier particles and the spurious particles distributed over the entire area, according to a second example of the invention.
Figure 5B:
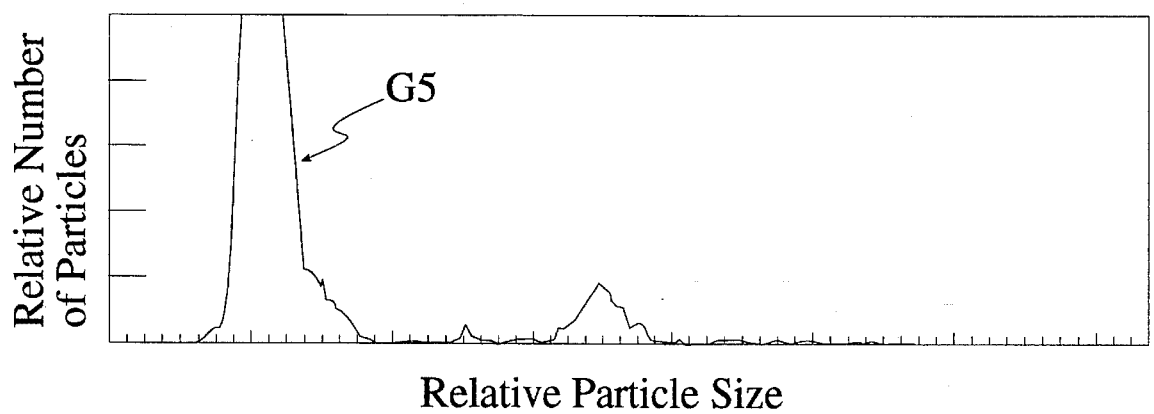
FIG. 5B is a distribution plot of only the carrier particles in the second example.

FIGS. 5A and 5B show the results of the application of the present invention when few spurious particles are present in the analyte. For this example, the analyte was prepared in the same manner as for FIGS. 4A and 4B. Curve G4 represents the total distribution of measured particles, including both the non-aggregated and aggregated insoluble carriers as well as spurious particles.

The size distribution of the spurious particles was then developed by interpolation as previously described and subtracted from curve G4 to develop corrected curve G5. It can now be seen that even though curves G4 and G5 are similar because of the small number of spurious particles in the analyte, the correction achieved for curve G5 is significant.

In curve G4, the degree of aggregation A was 1.08% and the AFP concentration of the analyte per unit volume was 2.70 ng/ml. In corrected curve G5, the degree of aggregation was 1.07% and the AFP concentration of the analyte was 2.68 ng/ml.

Figure 6A:
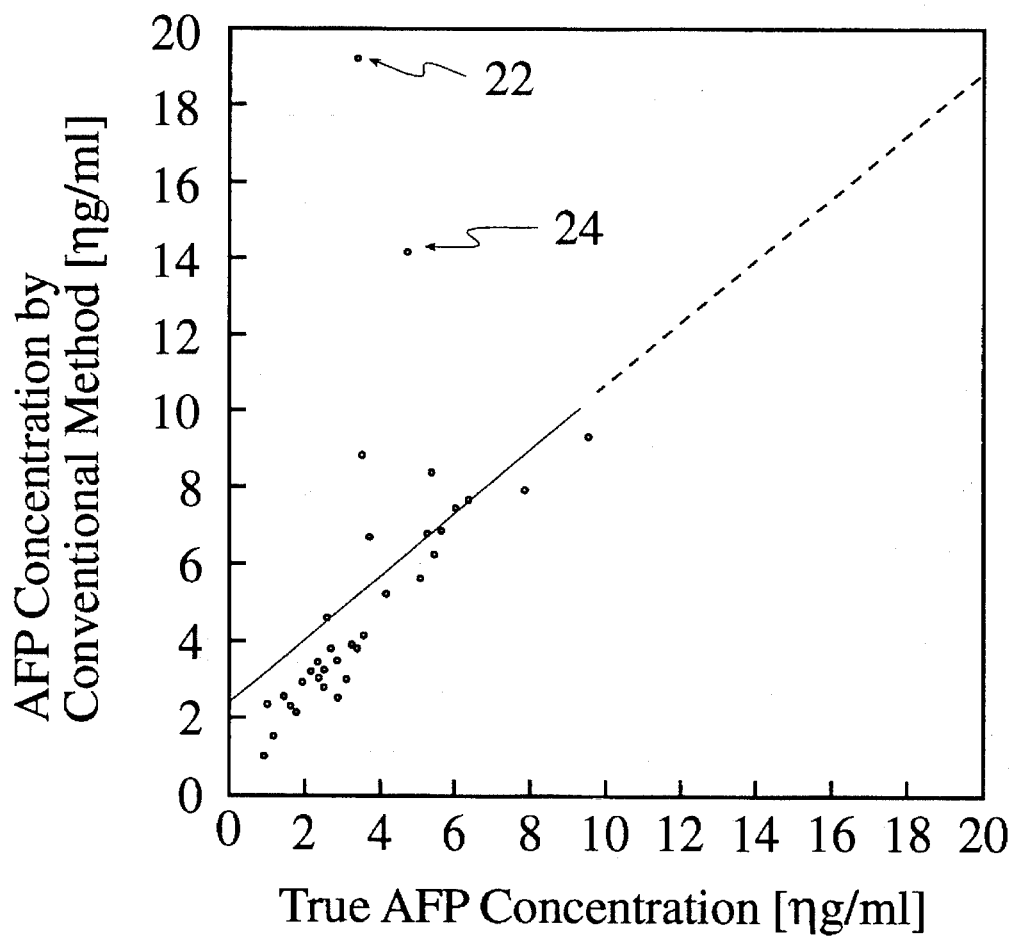
FIG. 6A is a relationship between an AFP concentration calculated by a conventional method and a true AFP concentration.

FIG. 6A is a graph showing the relationship an AFP concentration prepared using conventional methods and a true AFP concentration. In this graph, the vertical axis (AFP concentration by conventional methods) represents the total concentration of non-aggregated and aggregated as well as spurious particles, as derived from a plurality (33) of samples. The horizontal axis represents a true AFP concentration. The true AFP concentration was prepared by centrifugal separation of the spurious particles in the sample and then removing them by filtration.

Figure 6B:
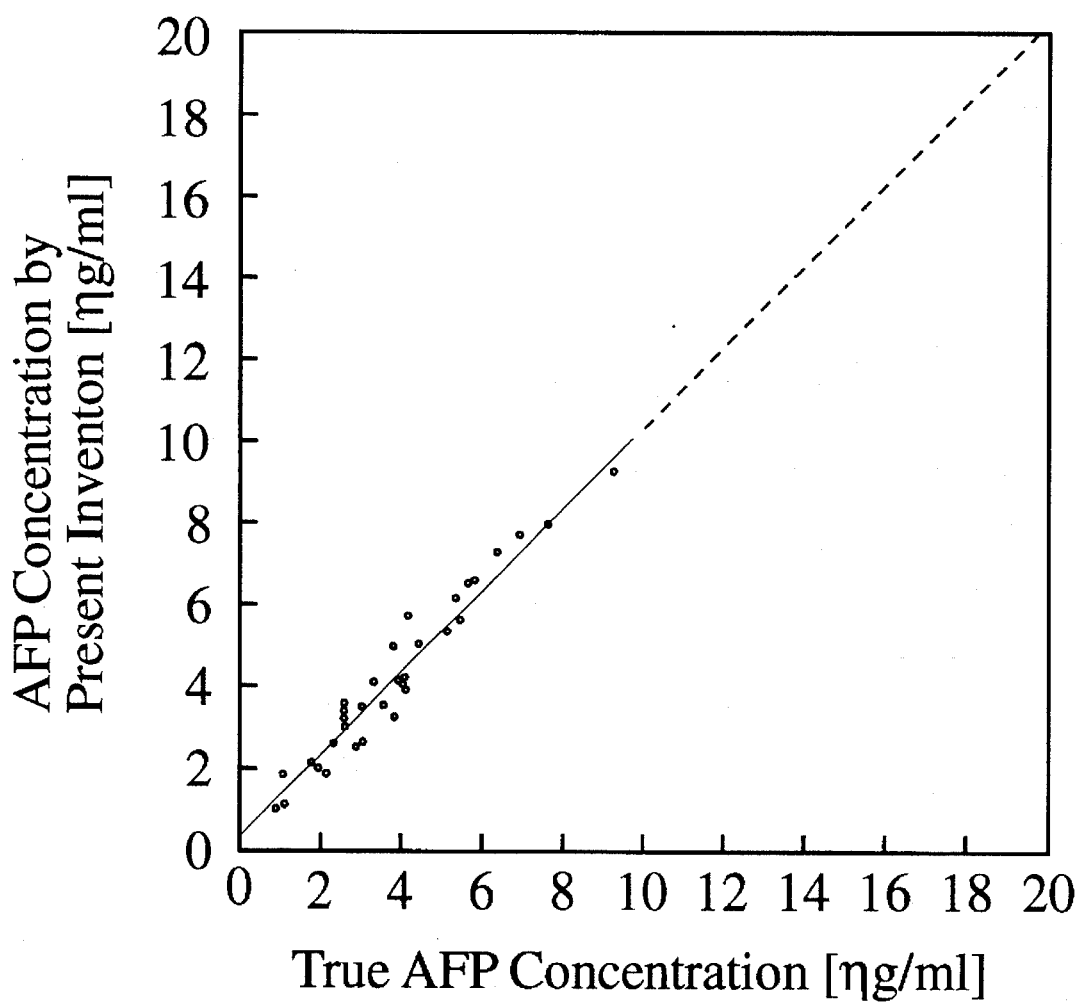
FIG. 6B is a relationship between an AFP concentration calculated by the examples of this invention and a true AFP concentration.

FIG. 6B is a graph showing the relationship between an AFP concentration prepared using the present invention, wherein the interpolated distribution of spurious particles is subtracted from the total distribution of particles.

Referring again to FIG. 6A, it is clear that the conventionally prepared concentration is irregular. Concentrations at 22 and 24 are completely off the straight line plot because of the presence of chylous particles. The correlation coefficient of this graph is 0.408. By comparison, the total distribution plot shown in FIG. 6B is close about the straight line plotted and the correlation coefficient of this graph is 0.964.

Figure 7A:
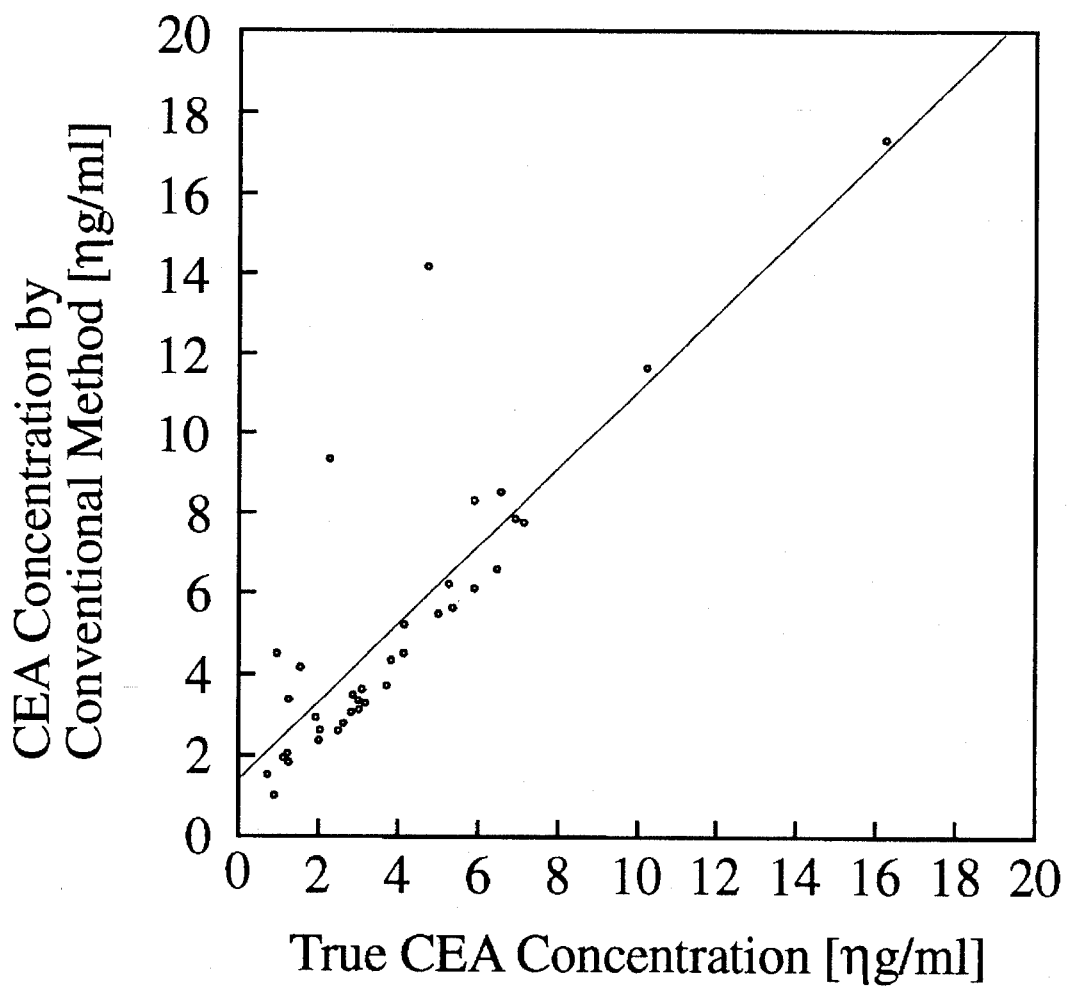
FIG. 7A is a relationship between a CEA concentration calculated by a conventional method and a true CEA concentration.

FIG. 7A, as in FIG. 6A, shows the relationship between a carcinoembrionic antigen (CEA) concentration prepared by conventional methods as described previously, including both non-aggregated and aggregated insoluble carriers and spurious particles and a true CEA concentration, including only non-aggregated and aggregated insoluble carriers.

The true CEA concentration was prepared by centrifugal separation of the spurious particles in the sample and then removing them by filtration.

Figure 7B:
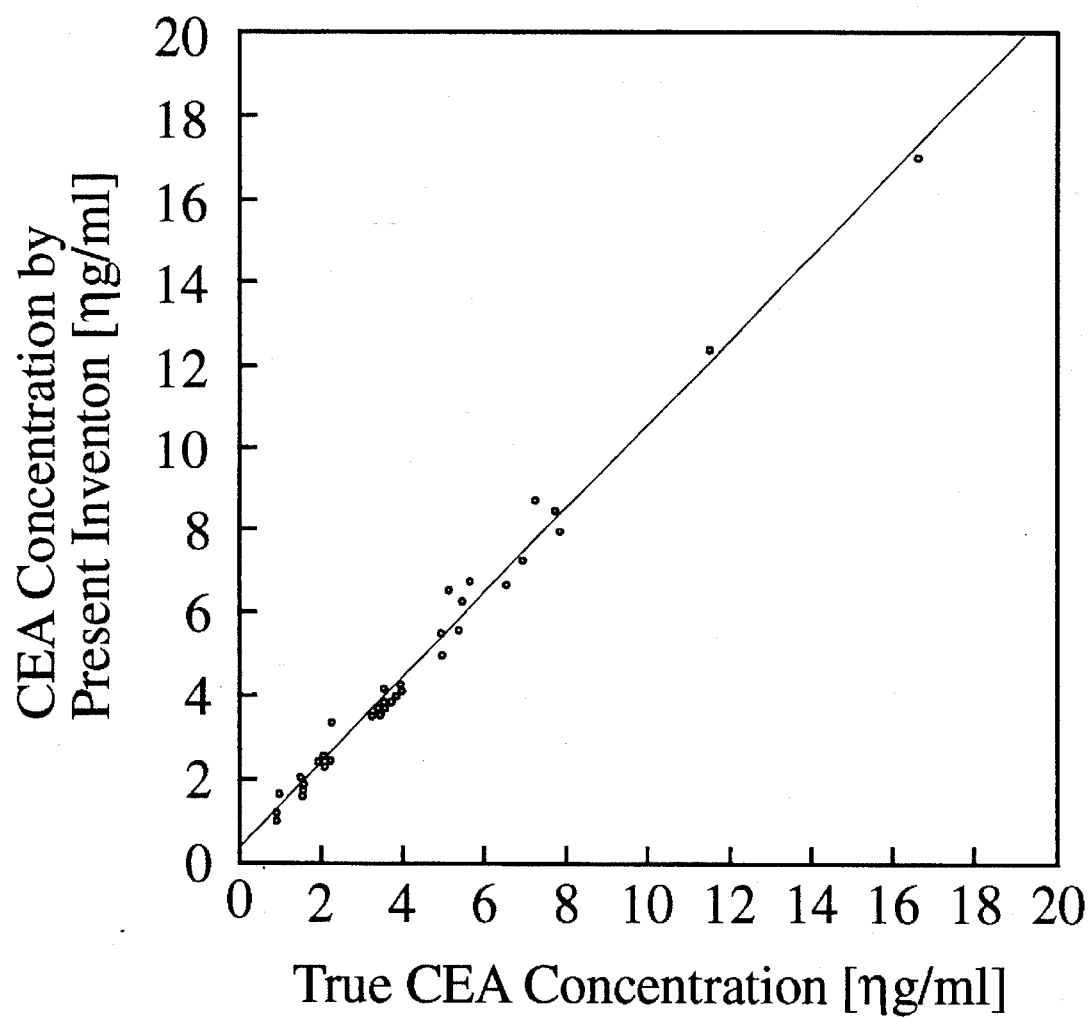
FIG. 7B is a relationship between a CEA concentration calculated by the examples of this invention and a true CEA concentration.

FIG. 7B, as in FIG. 6B, shows the relationship of a CEA concentration prepared using the present invention, wherein the spurious particles interpolated are subtracted from the total particles detected, and a true CEA concentration.

A comparison between FIGS. 7A and 7B also shows the improvements in accuracy realized with the present invention. In FIG. 7A, CEA concentrations developed conventionally are well off the straight line plotted with a correlation coefficient of 0.824. The CEA concentrations derived using the present invention are all along the straight line plotted, with a correlation coefficient of 0.992.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A process for determining a concentration of an analyte in a sample by antigen/antibody reaction mediated particle agglutination in the presence of spurious particles comprising the steps of:

providing a reaction mixture;

said reaction mixture including an analyte having a concentration and insoluble particles sensitized with one of an antibody against said analyte or an antigen against said analyte;

aggregating said insoluble particles responsively to said concentration;

detecting total particles in said reaction mixture to produce a particle detection signal;

said particle detection signal being responsive to a first size distribution of said total particles in said reaction mixture;

said total particles including aggregated said insoluble particles, non-aggregated said insoluble particles, and spurious particles;

determining from said particle detection signal said first size distribution of said total particles in said reaction mixture;

determining a second size distribution of said spurious particles within said first size distribution of said total particles;

subtracting said second size distribution from said first size distribution to produce a corrected size distribution of said insoluble particles; and determining said concentration of said analyte from said corrected size distribution.

2. The method according to claim 1, wherein the step of determining said second size distribution of spurious particles includes:

providing a range of sizes, said range being equivalent to all known sizes of said insoluble particles;

indicating a first portion of said first size distribution that intercalates or is smaller than said range of sizes;

indicating a second portion of said first size distribution that is a largest one size range of said range of sizes;

fitting a curve by interpolating said first portion across said range to yield a part of said second size distribution;

measuring a number of particles in said second portion at a time before insoluble particles can be aggregated, to determine a second portion spurious particle distribution; and combining said part of said second size distribution with said second portion spurious particle distribution to yield said second size distribution.

3. The method of claim 2 wherein the step of fitting a curve by interpolating includes fitting a curve using a cubic spline function.

* * * * *